US008361440B2

(12) United States Patent
Peter

(10) Patent No.: US 8,361,440 B2
(45) Date of Patent: Jan. 29, 2013

(54) IMAGING METHOD AND DEVICE FOR CARRYING OUT SAID METHOD

(75) Inventor: Jörg Peter, Heidelberg (DE)

(73) Assignee: Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 561 days.

(21) Appl. No.: 10/517,637

(22) PCT Filed: Jun. 11, 2003

(86) PCT No.: PCT/EP03/06102
§ 371 (c)(1),
(2), (4) Date: Apr. 11, 2005

(87) PCT Pub. No.: WO03/104799
PCT Pub. Date: Dec. 18, 2003

(65) Prior Publication Data
US 2005/0215873 A1  Sep. 29, 2005

(30) Foreign Application Priority Data
Jun. 11, 2002 (DE) .................................. 102 25 932

(51) Int. Cl.
*A61K 49/00* (2006.01)
(52) U.S. Cl. .......................................... 424/9.1; 600/407
(58) Field of Classification Search .................. 600/407, 600/408, 425–429, 414, 410, 420, 424, 431, 600/436; 424/9.1, 1.11, 9.6
See application file for complete search history.

(56) References Cited

U.S. PATENT DOCUMENTS
4,969,175 A * 11/1990 Nelson et al. ................. 378/146
5,301,673 A * 4/1994 Rabito et al. ................. 600/436
(Continued)

FOREIGN PATENT DOCUMENTS
WO   WO 01/56582 A   8/2001

OTHER PUBLICATIONS
David P. McElroy et al., "Evaluation of A-SPECT: A Desktop Pinhole SPECT System for Small Animal Imaging", Proc. Med. Imag. Conf., San Diego, 2001, 5 pages.
(Continued)

*Primary Examiner* — Elmer Chao
(74) *Attorney, Agent, or Firm* — Foley & Lardner LLP

(57) ABSTRACT

The invention relates to an imaging method for simultaneously determining in vivo distributions of bioluminescent and/or fluorescent markers and radioactive markers at identical projection angles, the distribution of the bioluminescent and/or fluorescent markers being determined by separate detection of photons having a first average energy, which are emitted by the bioluminescent and/or fluorescent markers, by means of at least one first detector and the distribution of the radioactive markers being determined by simultaneous separate detection of photons having a second average energy, which are emitted by the radioactive markers, by means of at least one second detector. Furthermore, it also relates to an apparatus for carrying out the imaging method, containing at least one CCD camera (1, 2) as first detector, at least one single photon emission computer tomography (SPECT) detector (3) as second detector and a layer (5), which essentially reflects the photons of the bioluminescent and/or fluorescent markers and essentially transmits the photons of the radioactive markers.

4 Claims, 6 Drawing Sheets

U.S. PATENT DOCUMENTS

Figure 1:
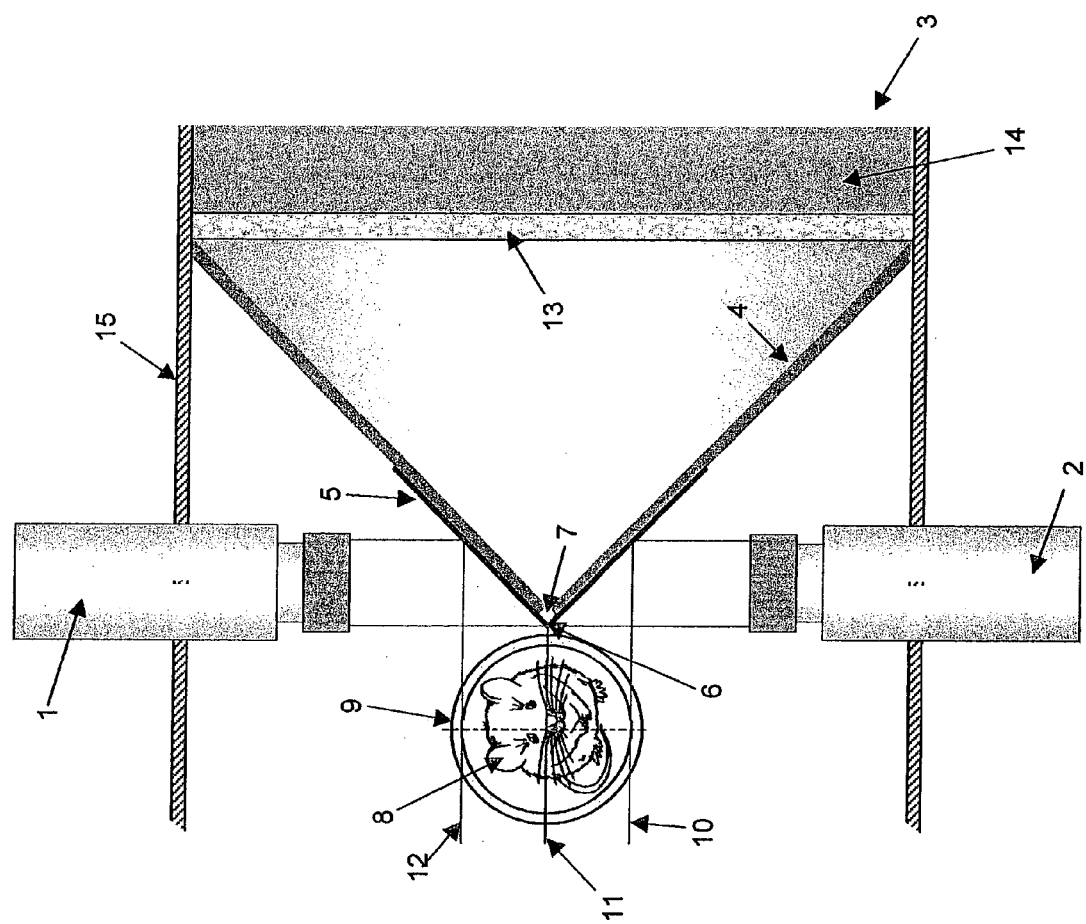

| | | | | |
|---|---|---|---|---|
| 5,647,363 | A | * | 7/1997 | Rabito et al. ............... 600/345 |
| 5,678,550 | A | * | 10/1997 | Bassen et al. .............. 600/431 |
| 6,232,107 | B1 | * | 5/2001 | Bryan et al. ................ 435/189 |
| 6,280,703 | B1 | * | 8/2001 | Combs et al. ................. 424/9.1 |
| 6,312,961 | B1 | * | 11/2001 | Voirin et al. ................ 436/518 |
| 6,596,257 | B2 | * | 7/2003 | Bryan ........................... 424/9.1 |
| 2002/0042566 | A1 | * | 4/2002 | Matsuzaki et al. ........... 600/407 |
| 2003/0101466 | A1 | * | 5/2003 | Turner ............................. 800/10 |

OTHER PUBLICATIONS

Andrew G. Weisenberger et al., "Development of a Novel Radiation Imaging Detector System for In Vivo Gene Imaging in Small Animal Studies", IEEE Transactions on Nuclear Science, Jun. 1998, pp. 1743-1749, vol. 45, No. 3.

Christoph Brerner etal., "In Vivo Imaging of Gene Expression: MR and Optical Technologies", Academic Radiology, Jan. 2001, pp. 15-23, vol. 8, No. 1.

Ralph Weissleder et al., "In vivo imaging of tumors with protease-activated near-infrared fluorescent probes", Nature Biotechnology, Apr. 1999, pp. 375-378, vol. 17.

Hooper C.E. et al., "CCD Imaging of Luciferase Gene Expression in Single Mammalian Cells", Journal of Bioluminescence and Chemiluminescence, 1990, pp. 123-130, vol. 5.

Jacobs A. et al., "Functional coexpression of HSV-1 thymidine Kinase and Green Fluorescent Protein: Implications for noninvasive imaging of transgene expression.", Neoplasia, Jun. 1999, pp. 154-161, vol. 1, No. 2.

Kost B. et al., "Non-destructive Detection of Firefly Luciferase (LUC) Activity in Single Plant Cells Using a Cooled, Slow-Scan CCD Camera and an Optimized Assay", Plant Journal, 1995, pp. 155-166, vol. 8, No. 1.

Edinger M. et al., Monitoring the anti tumor activity of expanded CD8 + NKT cells after allogeneic bone marrow transplantation using bioluminescent imaging, Blood, Nov. 16, 2001, p. 433a, vol. 98, No. 11, parts 1 and 43$^{rd}$ Annual Meeting of the American Society of Hematology, Part 1, Orlando, Florida, Dec. 7-11, 2001.

Ebmeier K.P. et al., Temporal lobe abnormalities in dementia and depression: a study using high resolution single photon emission tomography and magnetic resonance imaging. Journal of Neurology, Neurosurgery and Psychiatry, Nov. 1997, pp. 597-604, vol. 63, No. 5.

Handler A.M. et al., Polyubiquitin-regulated DsRed marker for transgenic insects., Biotechniques, Oct. 2001, pp. 820, 824-828, vol. 31, No. 4.

Rogus R.D., et al., "Accuracy of a photogrammetry-based patient positioning and monitoring system for radiation therapy.", Medical Physics, May 1999, pp. 721-728, vol. 26, No. 5.

Edinger M. et al., "Advancing animal models of neoplasia through in vivo bioluminescence imaging.", European Journal of Cancer, Nov. 1992, pp. 2128-2136, vol. 38, No. 16.

Edinger M. et al., "Revealing Lymphoma growth and the efficacy of immune cell therapies using in vivo bioluminescence imaging.", Blood, Jan. 15, 2003, pp. 640-848, vol. 101, No. 2.

* cited by examiner

IMAGING METHOD AND DEVICE FOR CARRYING OUT SAID METHOD

The invention relates to an imaging method for determining in vivo distributions of bioluminescent, fluorescent and radioactive markers. Furthermore, it relates to an apparatus for carrying out the imaging method.

The qualitative and quantitative detection of morphological, functional and biochemical parameters using imaging methods is the basis of diverse fields of medical research and application. Known imaging methods used in tumor research, inter alia, are, by way of example, single photon emission computer tomography (SPECT) using radionuclides or optical technologies using fluorescence or bioluminescence.

In the case of single photon emission computer tomography, radioactive markers are injected into the animal or human to be examined, which markers concentrate in specific organs or tissue types of the animal/human depending on the biological carriers which transport them. The radioactive markers emit radioactive radiation (γ radiation), the intensity of which in a specific region of the subject to be examined depends on the concentration of the marker in said region. The radioactive radiation is detected by means of a γ camera or scintillation camera. For carrying out high-resolution studies on small laboratory animals, apparatuses for detecting the γ photons are disclosed for example in D. P. McElroy et al.: Evaluation of A-SPECT: A Desktop Pinhole SPECT System for Small Animal Imaging, Proc. Med. Imag. Conf. San Diego 2001, M10-4 or in A. G. Weisenberger et al.: Development of a Novel Radiation Imaging Detector System for In Vivo Gene Imaging in Small Animal Studies, IEEE Transactions on Nuclear Science, Vol. 45, No. 3 (June 1998) 1743-1749. Examples of fields of application for such tomographs are preclinical research or radiotracer development.

A further imaging method known in the prior art for in vivo examination is an optical method that makes use of fluorescent or bioluminescent markers. The latter serve for example as reporter genes which are used for observing gene expression since the associated proteins produce a measurable optical signal. The gene that codes for the protein luciferase is a much used reporter gene. In this case, the gene for a specific protein is replaced by the luciferase gene. Upon activation of the associated promoter, the latter then drives the transcription of the luciferase gene. The enzyme luciferase from the North American firefly *Photinus pyralis* catalyzes the oxidative decarboxylation of luciferin in the presence of ATP and $Mg^{2+}$. This gives rise to flashes of light which accumulate to form the light emission from these animals. The luminescence occurring in the presence of luciferin and ATP consequently indicates the expression of luciferase. This optical signal can easily be measured, for example by means of CCD cameras. In the same way as bioluminescent reporter genes, fluorescent reporter genes are used as well, for example the gene for the green fluorescent protein (GFP). Such proteins are stimulated into fluorescence by irradiation with an external light source. In vivo imaging of gene expression by optical methods is disclosed for example in C. Bremer, R. Weissleder: In Vivo Imaging of Gene Expression: MR and Optical Technologies, Academic Radiology, Vol. 8, No. 1 (January 2001) 15-23. These methods are also used, inter alia, for in vivo tumor monitoring (R. Weissleder et al.: In Vivo Imaging of Tumors with Protease-Activated Near-Infrared Fluorescent Probes, Nature Biotechnology, Vol. 17 (April 1999) 375-378).

Advantages of the molecules which emit the optical (fluorescence or luminescence) photons are, inter alia, that they have specific chemical properties of medical interest that are lacking in the radioactively marked components, for example that they can be activated by specific enzymatic interactions. By contrast, the radioactive substances have the advantage that the γ rays that they emit have much lower probabilities of interaction with dense tissue than the optical photons, so that they can penetrate through large tissue volumes or thicknesses. Furthermore, their slight or lack of interaction with the biochemical properties of the tissue to be examined may be advantageous. In the prior art, both imaging methods, the method for detecting the optical photons emitted by the fluorescent or luminescent molecules, on the one hand, and the method for detecting the higher-energy photons emitted by the radioisotopes, on the other hand, are carried out separately, in different apparatuses. A comparison of the images obtained by the two imaging methods is possible only to a limited extent since they cannot be obtained simultaneously and at the same projection angles. The problems of excessive burdening of the subject to be examined, the non-reproducibility of kinetic studies, the non-identical imaging geometries, animal and organ movement and the correct superposition of the images arise when the two methods are carried out successively.

Therefore, the present invention is based on the object of avoiding the disadvantages of the prior art and of combining the advantages of the two technologies described above.

This object is achieved by means of an imaging method for simultaneously determining in vivo distributions of bioluminescent and/or fluorescent markers and radioactive markers at identical projection angles, the distribution of the bioluminescent and/or fluorescent markers being determined by separate detection of photons having a first average energy, which are emitted by the bioluminescent and/or fluorescent markers, by means of at least one first detector and the distribution of the radioactive markers being determined by simultaneous separate detection of photons having a second average energy, which are emitted by the radioactive markers, by means of at least one second detector.

In this connection, projection is to be understood as the two-dimensional imaging of a three-dimensional energy distribution at a specific projection solid angle of the detector with respect to the object to be imaged. In the invention, the projection solid angles of the two detector systems with respect to the object are identical, that is to say that the object is "viewed" by both detectors from an identical projection angle.

Optical photons of the bioluminescent and/or fluorescent markers have a (first) average energy in the range between 1 eV and 3 eV. Photons of the radioactive markers have a second average energy in a range between 10 keV and 600 keV. The imaging method according to the invention is carried out in vivo. It may be applied to living laboratory animals, by way of example. In this case, it is advantageously possible

- to observe transport, metabolism and excretion of active substances in the living organism, and
- to measure biological processes in their natural environment.

In a preferred embodiment of the present invention, the photons of the bioluminescent and/or fluorescent markers having the first average energy and the photons of the radioactive markers having the second average energy are separated for the separate detection with the aid of a layer, the layer essentially reflecting or transmitting the photons in a manner dependent on their energy. By way of example, γ radiation is transmitted without or with only slight interactions with the layer, while the lower-energy optical radiation is reflected by the layer. This enables separate detection of the photons having different energies which are emitted at the same projection angle by markers in the subject to be examined.

In a preferred embodiment of the present invention, the layer serves for reflecting the photons of the bioluminescent and/or fluorescent markers in the direction of the at least one first detector and for transmitting the photons of the radioactive markers in the direction of the at least one second detector. Consequently, the photons having different energies are not only separated by the layer but are also already "steered" in the direction of the detectors that detect them.

Preferably, the bioluminescent and/or fluorescent markers comprise at least one marker from the group consisting of the markers of the luciferase reporter, the marker molecules having emission wavelengths in the near infrared range (NIRF molecules) and the molecules of the GFP (green fluorescent protein). Markers from this group have already been successfully integrated in the reporter gene concept and detected in vivo (in living) animals. The luciferase produces a blue or yellow-green light in the context of an enzymatic reaction (see above). The enzyme substrates that form the starting substances for the light-emitting products are called luciferins. Luciferase/luciferin systems are found for example in the firefly *Photinus pyralis* (emission maximum at 562 nm), in fireflies and in numerous luminous marine bacteria (emission maximum at 489 nm).

The green fluorescent proteins (GFP) which are characterized the best originate from the Pacific jellyfish *Aequorea victoria* and the sea pansy *Renilla reniformis*. In both cases, the GFP transforms blue chemiluminescence into green fluorescence (emission maximum at 508 µm). GFP is a relatively small protein, consisting of 238 amino acids.

The molecules having emission wavelengths in the near infrared range (NIRF markers) have lower probabilities of interaction in the tissue than photons having wavelengths in the visible wavelength spectrum and therefore a greater penetration depth.

By way of example, proteins, lipids, RNA or DNA can be marked by the bioluminescent and/or fluorescent markers or by the radioactive markers.

Preferably, the radioactive markers comprise at least one marker from the group As-72, Br-75, Co-55, Cu-61, Cu-67, Ga-67, Gd-153, I-123, I-125, I-131, In-111, Ru-97, Tl-201, Tc-99m and Xe-133. The radioisotope respectively used is selected as a marker with regard to its half-life and the energy of the radiation that it emits, in a manner dependent on the biological process to be measured.

In a preferred embodiment of the present invention, the detection of the photons having the first average energy is carried out by means of at least one CCD camera and the detection of the photons having the second average energy is carried out by means of at least one single photon emission computer tomography (SPECT) detector comprising a collimator with at least one aperture.

CCDs (charge coupled devices) are charge coupled imaging sensors that serve for highly sensitive detection of photons. The CCD camera is divided into a multiplicity of small light-sensitive zones (pixels) which produce the individual points of an image. The grid of pixels is formed by a circuit structure on a semiconductor crystal (usually silicon). The method of operation of the CCD camera is based on the liberation of electrons by impinging light in the semiconductor material. A photon falling onto a pixel liberates at least one electron that is held fixed by an electrical potential at the location of the pixel. The number of electrons liberated at the location of the pixel is proportional to the intensity of the light incident at said location. The number of electrons is measured in each pixel, with the result that an image can be reconstructed. CCDs should be cooled since otherwise more electrons would be read out which would not be liberated as a result of the light incidence but rather as a result of heating. In the case of the present invention, the optical photons of the bioluminescent and/or fluorescent markers are preferably detected with the aid of at least one CCD camera.

SPECT detectors usually contain γ or scintillation cameras. A scintillator absorbs the γ rays emitted by the radioisotopes. As a response thereto, the scintillator emits light scintillations comprising visible light which are detected by a group of photo-multipliers of the SPECT detector and converted into a measurable electrical signal. The location of the radioactive emission of photons in a body can be localized only when a collimator is arranged between the body and the scintillator. Said collimator serves for shielding from the scintillator photons which are not situated in an acceptance region defined by the collimator geometry. Furthermore, the collimator defines the field of view of the detector system.

The present invention furthermore relates to an apparatus for carrying out the imaging method according to the invention. Said apparatus contains at least one cooled CCD camera as first detector, at least one single photon emission computer tomography (SPECT) detector as second detector and a layer, which essentially reflects the photons of the bioluminescent and/or fluorescent markers and essentially transmits the photons of the radioactive markers. The layer serves (as already mentioned above) for separating the photons having different energies which are detected in different detectors (CCD camera and SPECT detector). The SPECT detector preferably comprises a collimator, a scintillator and a multiplicity of photomultipliers with associated electronic elements.

In the case of the present invention, the detectors and the layer are preferably fixedly installed in a predetermined spatial arrangement in a common housing. Since CCDs are insensitive to the energy spectrum of the photons emitted by the radionuclides, no shielding is necessary and the CCDs can be completely integrated in the tomograph that is shielded overall.

Depending on the arrangement of the detectors, a highly reflective or a diffusely reflective layer is used in the case of the present invention. As a highly reflective layer, by way of example, aluminum is vapor-deposited onto a suitable base material having a low attenuation coefficient. Such layers are available in the prior art. Diffusely reflective thin layers are equally obtainable in the prior art, for example in the form of micrograms of plastic applied to a suitable base material. In the case of the present invention, the layers are intended to be as thin as possible in order to ensure a minimum attenuation and scattering of the radioisotopic photons, so that these effects are negligible, in principle. If they are present at all, scattering and absorption by the layer can be compensated for in an image reconstruction following the detection. The minimum thickness is determined by the required static properties, for example the planar stiffness.

In a preferred embodiment of the present invention, the at least one SPECT detector comprises an (e.g. planar) scintillation crystal array with a multiplicity of scintillation crystals and a spatially resolving photomultiplier array. The scintillation crystals are dense, transparent crystalline materials (for example NaI(Tl)) that serve as converters for high-energy γ rays into visible light. The visible light is detected in the form of electrical signals in spatially resolving fashion by the photomultiplier array.

The present invention furthermore relates to an imaging method for alternately determining in vivo distributions of bioluminescent and/or fluorescent markers and in vivo distributions of radioactive markers by means of a common measurement setup at identical projection angles, the distribution of the bioluminescent and/or fluorescent markers being determined by separate detection of photons having a first average energy, which are emitted by the bioluminescent and/or fluorescent markers, by means of at least one first detector and, alternately with respect thereto, the distribution of the radioactive markers being determined by separate detection of photons having a second average energy, which are emitted by the radioactive markers, by means of at least one second detector.

In order to carry out this method according to the invention, use is preferably made of an apparatus in which the masks serving as collimators for the SPECT detectors, during a measurement, can be moved out of the fields of view of the CCD cameras and can be moved into the fields of view again.

If the masks are in this case situated outside the fields of view of the CCD cameras, then the sensitivity of these optical imaging systems is significantly increased. The detection of radioisotopic photons is not possible, however, in this state (without collimation). Therefore, the SPECT detectors are preferably inactive in the case of masks removed from the beam path. If the masks are situated in the beam path, then the CCD cameras are preferably inactivated. Temporally alternating introduction of the masks into the two positions (within/outside the field of view of the CCD cameras) results in a preferred application mode of the apparatus according to the invention.

The present invention is preferably used for in vivo studies of small animals (for example mice or rats), for in vivo observation of gene expression and for breast, prostate, skin tumor and thyroid gland imaging.

The present invention is explained in greater detail below with reference to the drawing.

Figure 2:
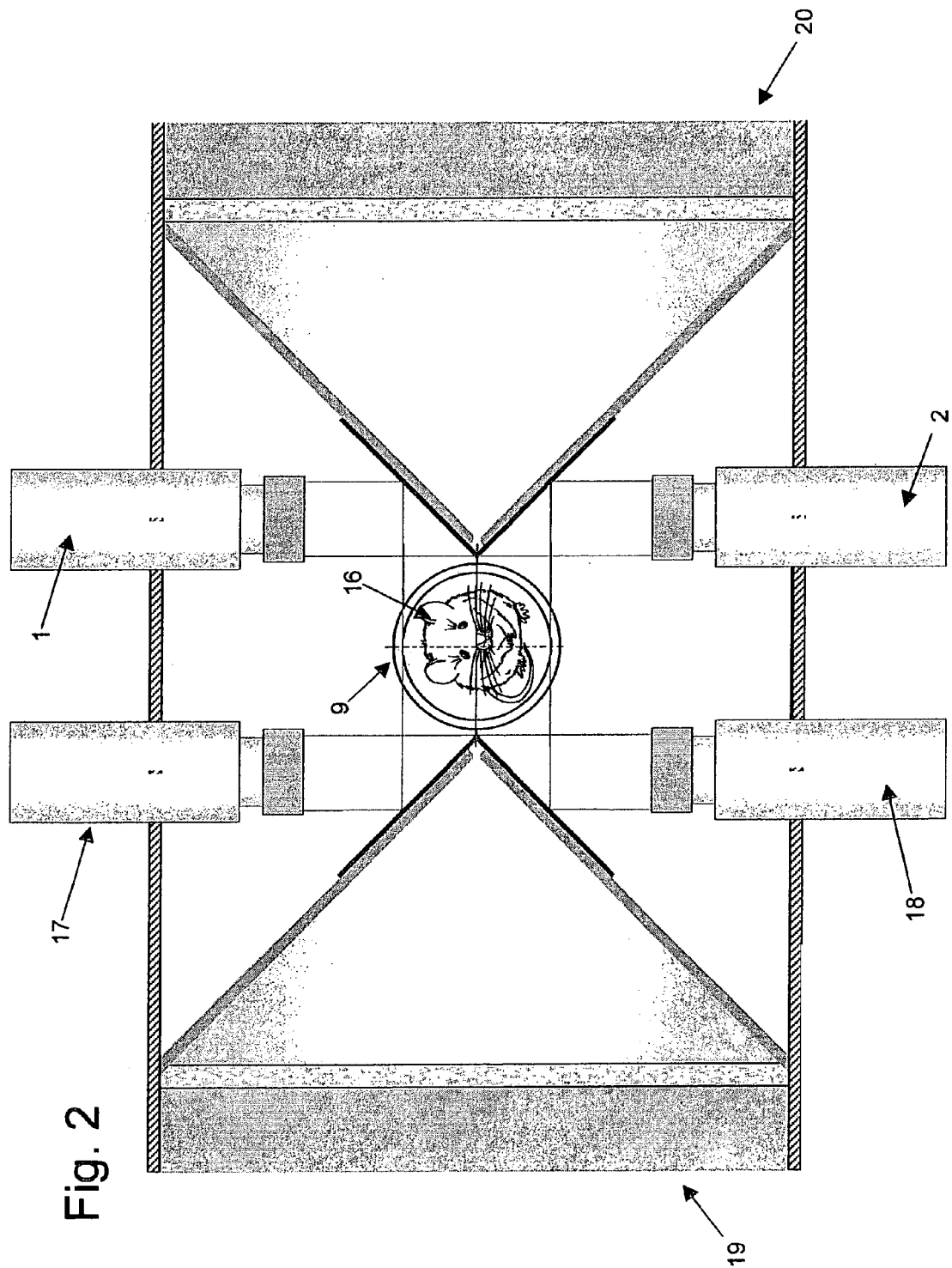
Figure 3:
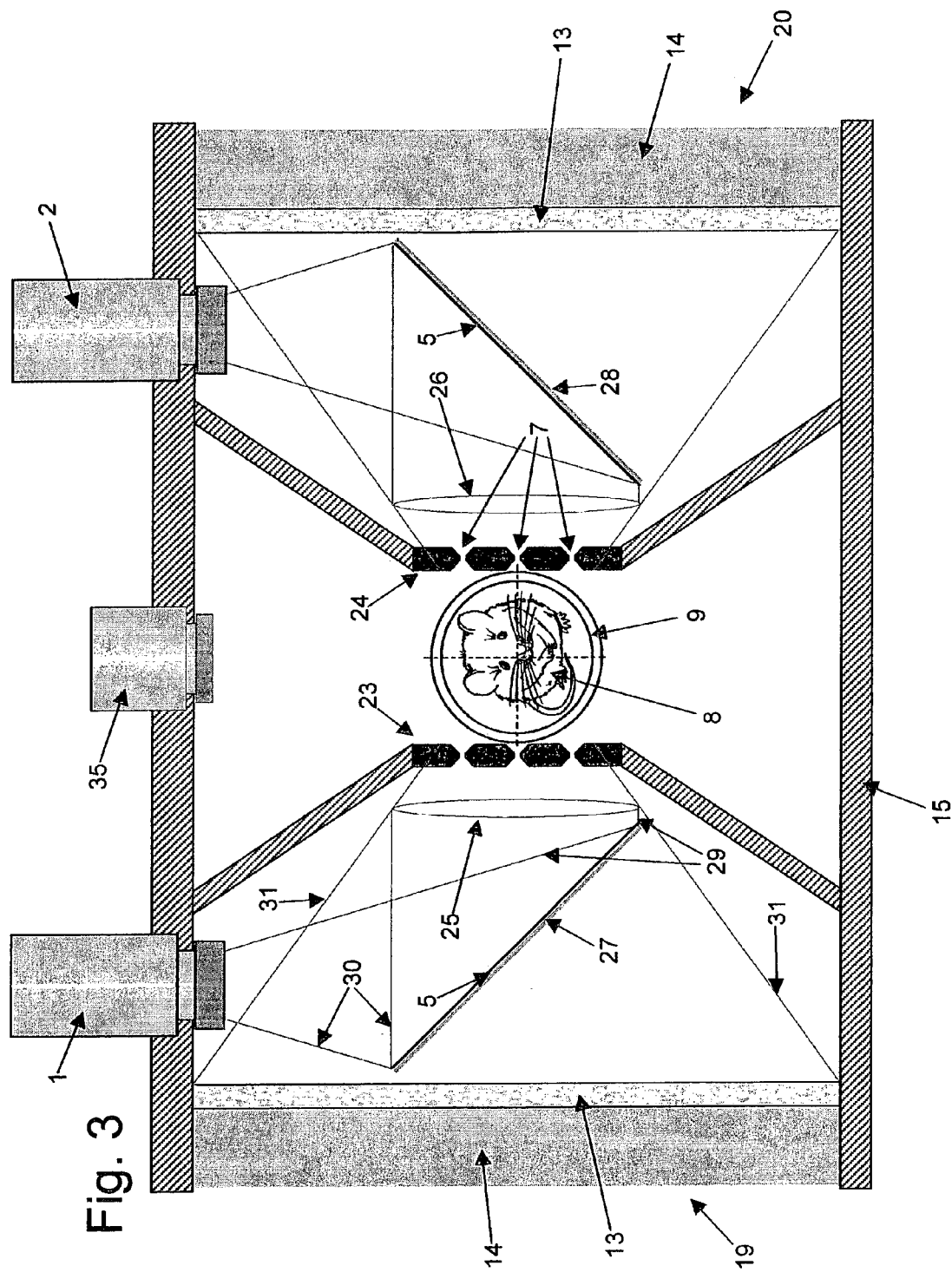
Figure 4:
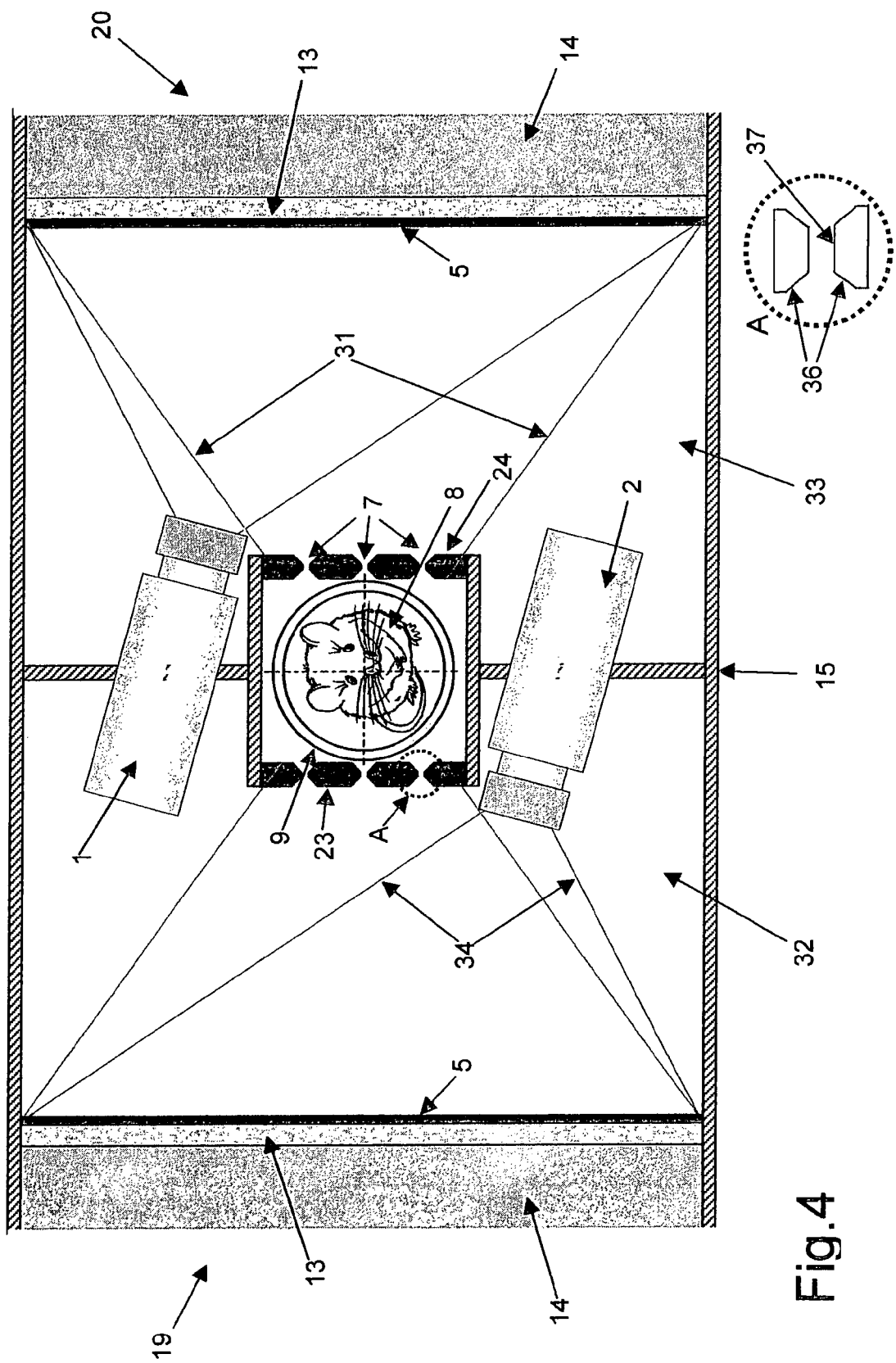
Figure 5:
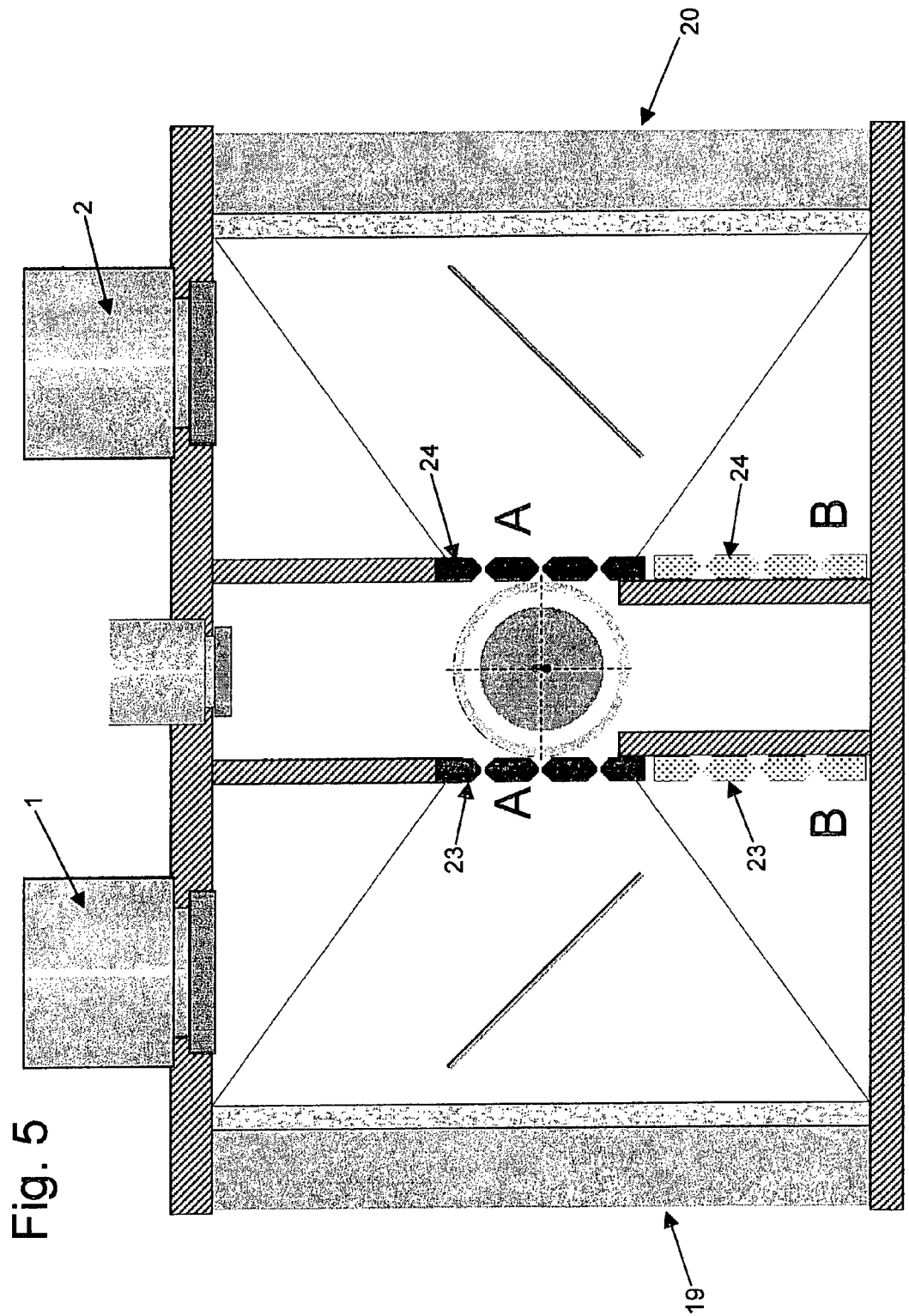
Figure 6:
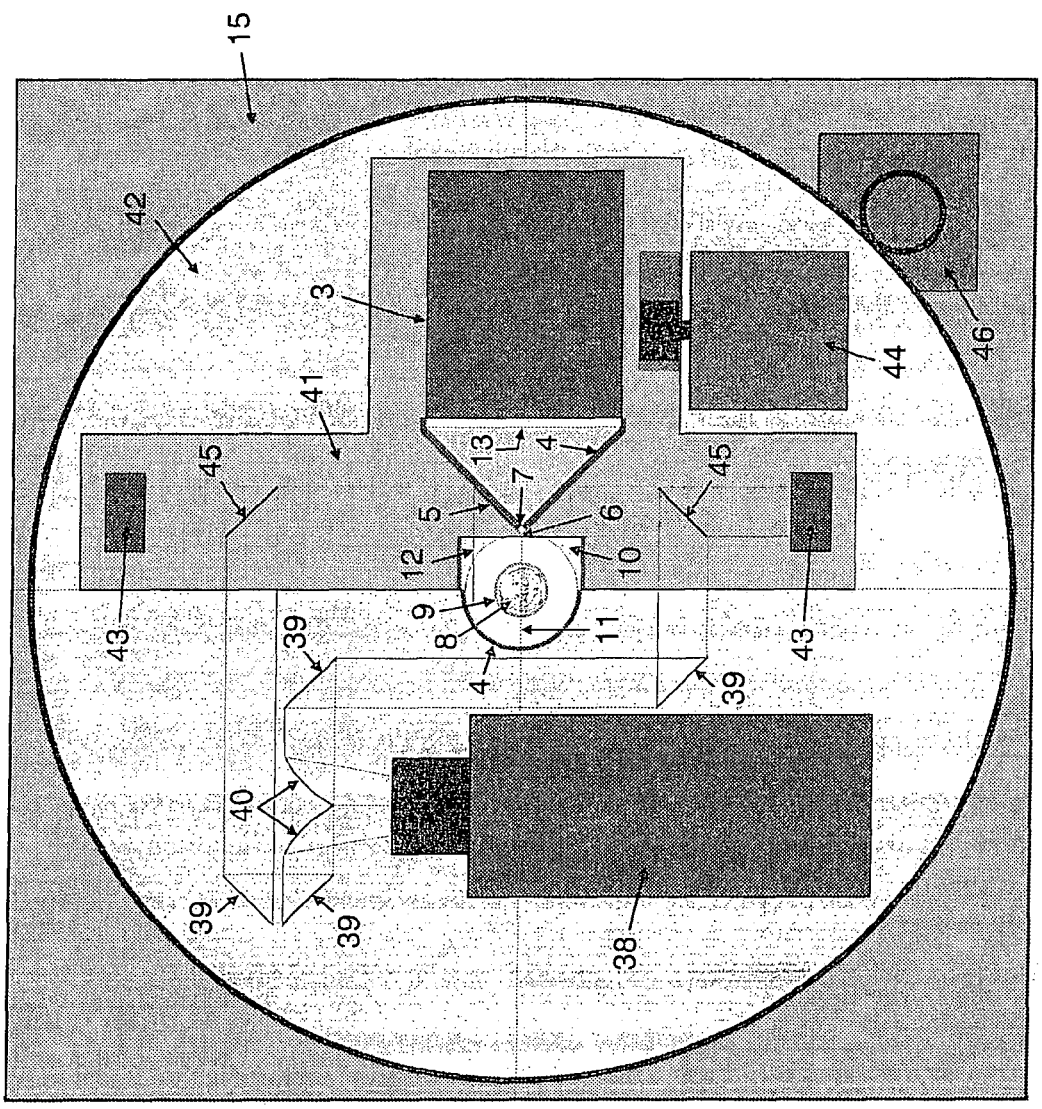

In the figures:

FIG. 1 shows a preferred embodiment of an apparatus according to the invention for carrying out the imaging method according to the invention, FIG. 2 shows a schematic illustration of the spatial arrangement of the detectors in a further possible embodiment of the apparatus according to the invention, FIG. 3 shows a further preferred embodiment of an apparatus according to the invention with two CCD cameras and two SPECT detectors, FIG. 4 shows a further embodiment of an apparatus according to the invention with two CCD cameras and two SPECT detectors, and FIG. 5 shows a modification of the embodiment of an apparatus according to the invention as shown in FIG. 3 with moveable masks, and FIG. 6 shows a preferred modification of the embodiment of an apparatus according to the invention as shown in FIG. 1 with just one CCD camera.

FIG. 1 shows a preferred embodiment of an apparatus according to the invention with two CCD cameras and one SPECT detector.

In the case of this preferred embodiment of the present invention, the apparatus according to the invention comprises two CCD cameras 1, 2 facing one another, an SPECT detector 3 arranged perpendicular to the CCD cameras 1, 2, a shielding 4 arranged in front of the SPECT detector 3 and bent at an angle of 90°, and a layer 5 fixed on the shielding 4 and likewise bent at an angle of 90°, the bending edge 6 of said layer lying on the bending edge of the shielding 4, the layer 5 covering an aperture 7 in the shielding 4. The layer 5 reflects optical photons, for example photons from bioluminescent and/or fluorescent markers, and transmits γ photons, for example photons from radioactive markers. The shielding 4 with the aperture 7 serves as a collimator for the SPECT detector 3. The subject to be examined (in this case the mouse 8), which is preferably situated in a thin-walled transparent tube 9 made of Plexiglas, is arranged as near as possible in front of said collimator. If the mouse 8 contains radioactive and bioluminescent and/or fluorescent markers and if said markers emit photons in the direction of the shielding 4, then the photons are largely reflected at the layer 5 or largely transmitted by the layer 5, depending on their energy. Three beam courses 10, 11, 12 are depicted in FIG. 1 for low-energy, optical radiation. The three beams 10, 11, 12 are reflected at an angle of 90° at the layer 5, with the result that they are steered directly to the CCD cameras 1, 2 and detected there. The medium- or high-energy γ photons can pass through the layer 5 without or with only slight interactions. They are then either absorbed by the shielding (for example made of lead or tungsten) or they pass through the aperture 7 into the SPECT detector 3, where they are detected. The SPECT detector comprises a scintillation crystal array 13 and a photomultiplier array 14, which transform the incident γ photons into optical photons and subsequently into an electric current. The SPECT detector 3 with the shielding 4 and the layer 5 and the CCD cameras 1, 2 are arranged fixedly in a housing 15, so that they maintain a specific spatial arrangement relative to one another. The housing 15 with the fixedly arranged elements can be rotated about the tube 9 with the mouse 8, preferably through 360°, in order to obtain measurement data at different angles. On the other hand, it is also conceivable to rotate the tube 9 together with the mouse 8 in the fixedly arranged housing 15.

The projection solid angle in FIG. 1 is 0 degrees by definition. The imaging planes of the detectors are parallel to one another (that is to say have the same projection angle of 0 degrees), although the imaging planes of the CCD cameras 1, 2 are rotated by respectively plus/minus 90 degrees with respect to the imaging plane of the SPECT system. Identical projection angles are provided because the fields of view (photon projection trajectories) of both CCDs 1, 2 experience a rotation through 90 degrees (through the reflective layer 5).

FIG. 2 shows a schematic illustration of the spatial arrangement of the detectors in a further possible embodiment of the present invention.

In this case, the design from FIG. 1 was adopted and also additionally constructed in mirrored fashion at an axial rotation axis running parallel to the CCD camera longitudinal axis centrally through the subject 16 that had been placed into a tube 9. Thus, photons emitted according to one direction can be detected by a first and a second CCD camera 1, 2 and a first SPECT detector 20 and photons emitted in the opposite direction can be detected by a third and fourth CCD camera 17, 18 and a second SPECT detector 19.

FIG. 3 shows a further preferred embodiment of an apparatus according to the invention with two CCD cameras and two SPECT detectors.

In the case of this preferred embodiment of the present invention, the apparatus according to the invention comprises two CCD cameras 1, 2 oriented in the same direction and spaced apart from one another; two SPECT detectors 19, 20 arranged perpendicular to the CCD cameras 1, 2, two masks 23, 24 with at least two apertures 7 in each case and two lenses 25, 26 between the two SPECT detectors 19, 20. Furthermore, the apparatus contains two reflectors 27, 28 essentially comprising a layer 5 in each case, which are oriented in such a way that they largely reflect, in the direction of the CCD cameras, the photons that are emitted by the bioluminescent and/or fluorescent markers, are transmitted through the apertures in the masks in the direction of the SPECT detectors and are focused by the lenses. The photons having different energy that are emitted by the bioluminescent and/or fluorescent and radioactive markers contained in the mouse 8 firstly have to pass through the masks 23, 24 with the apertures 7, said masks serving as SPECT collimators. Afterward, the optical photons are focused by the lenses 25, 26 onto the layer 5 of the respective reflector 27, 28, reflected at the highly reflective layer 5 in the direction of the respective CCD camera 1,2 and detected there. The beam course of two optical beams 29, 30 is depicted in FIG. 3. The γ photons interact scarcely or not at all with the lenses 25, 26 and the reflectors 27, 28, so that they can propagate in the acceptance cone 31 of the apertures 7 unimpeded in the direction of the scintillation crystal array 13 of the respective SPECT detector 19, 20 in which they are detected. Scattering and absorption (if present) caused by the lenses 25, 26 and layers 5 can be compensated for in a mathematical image reconstruction following the acquisition. The lenses 25, 26 preferably consist of materials having a low attenuation coefficient for the radioisotopic photons, for example Plexiglas.

The entire rigid arrangement combined in the housing 15 (CCD cameras 1, 2, reflectors 27, 28, lenses 25, 26, masks 23, 24 and SPECT detectors 19, 20) can be rotated around the tube 9, preferably through 360°, in order to be able to obtain a series of measurement data at identical angular distances all around the subject to be examined.

In principle, only half of the apparatus illustrated in FIG. 3 also suffices for examining the mouse 8, that is to say a CCD camera 1, a mask 23, an SPECT detector 19, a lens 25 and a reflector 27 with a layer 5. The double arrangement shown in FIG. 3 has the advantage, however, that in the case of tomographic application of the design, the sensitivity of the camera system is twice as high for the same acquisition.

The apparatus according to the invention as illustrated in FIG. 3 optionally comprises a position sensor 35 for determining the current position of the mouse, which possibly moves in the tube 9 during a measurement. An optical (standard) positioning system that continuously records the position of markers fitted externally to the mouse is involved in this case. This additional positioning system is necessary only when the mouse is permitted to move in the tube 9, since it is then not possible to exactly derive (and compensate for) the movement of the animal from the distributions acquired in vivo.

FIG. 4 shows a further embodiment of an apparatus according to the invention.

In the case of this preferred embodiment of the present invention, the apparatus according to the invention comprises two CCD cameras 1, 2 oriented parallel and oppositely to one another, between two SPECT detectors 19, 20 facing one another and two masks 23, 24 with at least two apertures 7 in each case, a respective layer 5 being situated in front of the SPECT detectors 19, 20, said layer largely reflecting the photons emitted by the bioluminescent and/or fluorescent markers and largely transmitting the photons emitted by the radioactive markers. In this case, the housing 15 is subdivided into two symmetrically constructed chambers 32, 33, in the center of which the subject (mouse 8) to be examined is situated in a tube 9, the entire arrangement combined in the housing 15 being mounted such that it can be rotated, preferably through 360°, about said subject. The masks 23, 24 are situated on opposite sides of the mouse 8, a portion of the photons emitted by the fluorescent, luminescent and radioactive markers passing through the apertures 7 of said masks into the acceptance cone 31 of the SPECT detectors. The photons of the radioactive markers pass largely without interaction through the layer 5 and are subsequently detected by the SPECT detector 19, 20. The photons having lower energy from the fluorescent or bioluminescent markers are largely reflected at the layer 5. The layer 5 preferably diffusely reflects the photons emitted by the bioluminescent and/or fluorescent markers, so that a portion of the reflected radiation is reflected in the direction of the CCD cameras 1, 2 and detected there. The field of view 34 of the CCD cameras is illustrated in FIG. 4.

In principle, only half of the apparatus illustrated in FIG. 4 also suffices for examining the mouse 8, that is to say a CCD camera 1, a mask 23 and an SPECT detector 20 with a diffusely reflective layer 5. The double arrangement shown in FIG. 4 has the advantage, however, of a higher measurement signal overall since the photons emitted in both directions are detected and, consequently, a higher resolution of the image is calculated therefrom.

FIG. 5 shows a modification of the embodiment of an apparatus according to the invention as shown in FIG. 3 with moveable masks.

In principle, the construction of this embodiment of an apparatus according to the invention corresponds to that shown in FIG. 3. In addition, in the case of this modification, the first and second masks 23, 24 are fixed in such a way that, during the acquisition, they can be lead out of the fields of view of the CCD cameras 1, 2 (from position A to position B) and be put back into the initial position (A) again. If the masks 23, 24 are situated outside the fields of view of the CCD cameras 1, 2 (position B), then the sensitivity of these optical imaging systems is significantly increased. The detection of radioisotopic photons is not possible, however, in this state (without collimation). Therefore, the SPECT detectors 19, 20 are inactive in the case of masks 23, 24 that are removed from the beam path. Lenses are not required in this embodiment of the present invention. The CCD cameras 1, 2 are provided with an optical arrangement for focusing the beams emitted by the bioluminescent and/or fluorescent markers. If the masks 23, 24 in the embodiment of the apparatus according to the invention as shown in FIG. 5 are in position A, then the CCD cameras 1, 2 are preferably inactivated. Temporally alternate introduction of the masks 23, 24 into the positions A and B results in a further preferred application mode of the design from FIG. 3.

FIG. 6 reveals a preferred modification of the embodiment of an apparatus according to the invention as shown in FIG. 1 with just one CCD camera.

The imaging principle as illustrated in FIG. 1 is adopted in the case of this preferred embodiment of the present invention. The construction and the method of operation of the SPECT camera 3, including the shielding 4, the aperture 7 and the arrangement and method of operation of the reflective layer 5, are identical to the apparatus described therein. In a departure, however, in accordance with this embodiment variant, the separate fields of view of the reflective layer 5 are defined by means of an arrangement of mirrors 39, 40, 45 in such a way that they are imaged in a manner adjoining one another in the objective of the CCD camera 38 and thus on the light-sensitive matrix. The mirrors 39 and 45 are preferably configured in planar fashion, while the mirrors 40 may be formed such that they are curved concavely. The mirrors 45 are transmissive on one side, so that laser beams can optionally be introduced in order to stimulate NIRF markers.

This type of projection assembly can be chosen since the spatial resolution of the CCD camera 38 is at least one order higher than the physically possible geometric resolution in the object, here the mouse 8, which is limited on account of photon scattering processes in the object 8. The advantage of this modification is an embodiment of the subject matter of the present invention which is of spatially more compact construction and less expensive.

In order to be able to optimally image animals of different sizes, in the embodiment variant illustrated in FIG. 6, the SPECT camera 3 including the shielding 4, the aperture 7 and the reflective surface 5 and also mirrors 45 and laser beam coupling-in arrangements 43 is mounted on a platform 41 that can be displaced by means of a stepper motor 44. The field of view imaging of the CCD camera 38 is defined such that the average imaging lengths of the two half-fields from the object 8 to the objective of the CCD camera 38 are of identical magnitude. This condition is also ensured when the radial position of the displaceable platform 41 with respect to the object 8 is changed. The platform 41 including all of the partial apparatuses mounted thereon, such as, by way of example, the stepper motor 44 required for the drive, the mirrors 39 and 40, the shielding 4 and also the CCD camera 38, are fixed on a rotatable mounting support 42. The mounting support 42 can be rotated through 360° by means of a stepper motor 46, so that the projection-identical fields of view of both camera systems can be arranged at any desired common projection angle with respect to the object 8 for the purpose of obtaining image data. While the mounting support 42 is accommodated in rotatable fashion on the housing 15, the stepper motor 46 is fixedly connected to the housing 15.

In all of the described embodiments of the present invention, the aperture or apertures is or are countersunk elongate opening(s). These countersunk openings have the appearance e.g. of the detail enlargement A of FIG. 4. In this case, the apertures narrow from the outside 36 to a specific diameter 37, which they then maintain as far as the center. This reduces the penetration of isotopic photons in the region of conically tapering aperture edges.

LIST OF REFERENCE SYMBOLS

1 First CCD camera
2 Second CCD camera
3 SPECT detector
4 Shielding
5 Layer
6 Bending edge of the layer
7 Aperture
8 Mouse
9 Tube
10 First beam course
11 Second beam course
12 Third beam course
13 Scintillation crystal array
14 Photomultiplier array
15 Housing
16 Subject
17 Third CCD camera
18 Fourth CCD camera
19 Second SPECT detector
20 First SPECT detector
23 First mask
24 Second mask
25 First lens
26 Second lens
27 First reflector
28 Second reflector
29 First optical beam
30 Second optical beam
31 Acceptance cone of the SPECT detectors
32 First chamber
33 Second chamber
34 Field of view of the CCD cameras
35 Position sensor
36 Narrowing of the aperture
37 Constant diameter in the center of the opening
38 Further CCD camera
39 Mirror, planar
40 Mirror, curved concavely
41 Platform, radially displaceable
42 Mounting support, rotatable
43 Laser beam coupling-in arrangement
44 1st stepper motor
45 Mirror, transmissive on one side
46 2nd stepper motor

The invention claimed is:

1. An imaging method, comprising:
conducting an imaging procedure by simultaneously determining in vivo distributions of bioluminescent and/or fluorescent markers and in vivo distributions of radioactive markers of an object at identical projection angles;
wherein the distributions of the bioluminescent and/or fluorescent markers are determined by a first separate detection of photons having a first average energy, which are emitted by the bioluminescent and/or fluorescent markers, by at least one first detector;
wherein the distributions of the radioactive markers are determined by a second separate detection of photons having a second average energy, which are emitted by the radioactive markers, by at least one second detector;
wherein the photons of the bioluminescent and/or fluorescent markers having the first average energy and the photons of the radioactive markers having the second average energy are separated for the separate detection with the aid of a layer, the layer essentially reflecting the photons of the bioluminescent and/or fluorescent markers and transmitting the photons of the radioactive markers;
wherein the layer is used to reflect the photons of the bioluminescent and/or fluorescent markers in a first direction of the at least one first detector and for transmitting the photons of the radioactive markers in-a second direction of the at least one second detector, wherein the first and second directions are different from each other;
wherein the first separate detection and the second separate detection occur simultaneously;
wherein the at least one first detector, the at least one second detector, and the layer are fixedly arranged in a predetermined specific spatial arrangement relative to each other;
wherein the at least one first detector, the at least one second detector, and the layer are fixedly arranged as a rigid arrangement within a common housing;
wherein the object is placed within the housing during the imaging procedure; and
creating a first projection image from the first separate detection and a second projection image from the second separate detection, wherein the first and second projection images are of two-dimensional images of three-dimensional energy distributions of the bioluminescent and/or fluorescent markers and the radioactive markers of the object.

2. The imaging method as claimed in claim 1, wherein in the steps of determining the in vivo distributions, the bioluminescent and/or fluorescent markers comprise at least one marker from the group consisting of the markers of luciferase reporters, the marker molecules having emission wavelengths in the near infrared range (NIRF molecules) and the molecules of GFP (green fluorescent protein).

3. The imaging method as claimed in claim 1, wherein in the steps of determining the in vivo distributions, the radioactive markers comprise at least one marker from the group As-72, Br-75, Co-55, Cu-61, Cu-67, Ga-67, Gd-153, I-123, I-125, I-131, In-111, Ru-97, Tl-201, Tc-99m and Xe-133.

4. The imaging method as claimed in claim 1, wherein the detection of the photons having the first average energy is carried out by at least one light detector camera providing the first detector and the detection of the photons having the second average energy is carried out by at least one single photon emission computer tomography (SPECT) detector providing the second detector comprising a collimator with at least one aperture.

* * * * *

UNITED STATES PATENT AND TRADEMARK OFFICE
CERTIFICATE OF CORRECTION

| | | |
|---|---|---|
| PATENT NO. | : 8,361,440 B2 | Page 1 of 1 |
| APPLICATION NO. | : 10/517637 | |
| DATED | : January 29, 2013 | |
| INVENTOR(S) | : Peter | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 795 days.

Signed and Sealed this
Twenty-sixth Day of May, 2015

Michelle K. Lee
*Director of the United States Patent and Trademark Office*